United States Patent [19]
Song et al.

[11] Patent Number: 6,107,074
[45] Date of Patent: Aug. 22, 2000

[54] TRAF2-ASSOCIATED PROTEIN KINASE AND ASSAYS

[75] Inventors: Yeong Song, S. San Francisco; Mike Rothe, San Mateo, both of Calif.

[73] Assignee: Tularik Inc., South San Francisco, Calif.

[21] Appl. No.: 09/434,065

[22] Filed: Nov. 5, 1999

Related U.S. Application Data

[60] Continuation of application No. 09/252,571, Feb. 18, 1999, Pat. No. 5,981,250, which is a division of application No. 08/677,862, Jul. 10, 1996, Pat. No. 5,874,230.

[51] Int. Cl.⁷ .............................. C12N 9/12; C07K 1/00
[52] U.S. Cl. ........................................... 435/194; 530/350
[58] Field of Search .............................. 435/194; 530/350

[56] References Cited

PUBLICATIONS

Kentrup et al. (1996) J. Biol. Chem 271, 3488–3495; "Dyrk, a Dual Specificity Protein Kinase with Unique Structural Features Whose Activity is Dependent on Tyrosine Residues between Subdomains VII and VIII"; see Figs. 1 and 2 of sequence data.

Cheng et al. Isolation and mapping of human chromosome 21 cDNA. Genomics 23, 75, 1994.

Frohman, M. in PCR Protocols: A Guide to Methods and Applications (1990) Innis, et al. Eds. pp. 28–38, Academic Press, Inc. San Diego Calif.

*Primary Examiner*—Rebecca E. Prouty
*Assistant Examiner*—M. Monshipouri
*Attorney, Agent, or Firm*—Richard Aron Osman

[57] ABSTRACT

The invention provides methods and compositions relating to a novel human tumor necrosis factor receptor associated factor number two associated kinase protein. The invention provides hybridization probes and primers capable of hybridizing with the disclosed gene, nucleic acids encoding the kinase, methods of making the kinase proteins, and methods of using the compositions in diagnosis and drug screening.

5 Claims, 1 Drawing Sheet

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 3218 base pairs
      (B) TYPE: nucleic acid
      (C) STRANDEDNESS: double
      (D) TOPOLOGY: linear (ii) MOLECULE TYPE: cDNA (xi) SEQUENCE DESCRIPTION: SEQ ID NO:1:

```
ATGGAGCTCC ACCGCGGTGG CGGCCGCTCT AGAACTAGTG GATCCCCCAT AGTTTTGCCG     60

CTGGACTCTT CCCTCCCTTC CCCCACCCCA TCAGGATGAT ATGAGACTTG AAAGAAGACG    120

ATGCATACAG GAGGAGAGAC TTCAGCATGC AAACCTTCAT CTGTTCGGCT TGCACCGTCA    180

TTTTCATTCC ATGCTGCTGG CCTTCAGATG GCTGGACAGA TGCCCCATTC ACATCAGTAC    240

AGTGACCGTC GCCAGCCAAA CATAAGTGAC CAACAGGTTT CTGCCTTATC ATATTCTGAC    300

CAGATTCAGC AACCTCTAAC TAACCAGGTG ATGCCTGATA TTGTCATGTT ACAGAGGCGG    360

ATGCCCCAAA CCTTCCGTGA CCCAGCAACT GCTCCCCTGA GAAAACTTTC TGTTGACTTG    420

ATCAAAACAT ACAAGCATAT TAATGAGGTT TACTATGCAA AAAAGAAGCG AAGACACCAA    480

CAGGGCCAGG GAGACGATTC TAGTCATAAG AAGGAACGGA AGGTTTACAA TGATGGTTAT    540

GATGATGATA ACTATGATTA TATTGTAAAA AACGGAGAAA AGTGGATGGA TCGTTACGAA    600

ATTGACTCCT TGATAGGCAA AGGTTCCTTT GGACAGGTTG TAAAGGCATA TGATCGTGTG    660

GAGCAAGAAT GGGTTGCCAT TAAAATAATA AAGAACAAGA AGGCTTTTCT GAATCAAGCA    720

CAGATAGAAG TGCGACTTCT TGAGCTCATG AACAAACATG ACACTGAAAT GAAATACTAC    780

ATAGTGCATT TGAAACGCCA CTTTATGTTT CGAAACCATC TCTGTTTAGT TTTTGAAATG    840

CTGTCCTACA ACCTCTATGA CTTGCTGAGA AACACCAATT TCCGAGGGGT CTCTTTGAAC    900

CTAACACGAA AGTTTGCGCA ACAGATGTGC ACTGCACTGC TTTTCCTTGC GACTCCAGAA    960

CTTAGTATCA TTCACTGTGA TCTAAAACCT GAAAATATCC TTCTTTGTAA CCCCAAACGC   1020

AGTGCAATCA AGATAGTTGA CTTTGGCAGT TCTTGTCAGT TGGGGCAGAG GATATACCAG   1080

TATATTCAGA GTCGCTTTTA TCGGTCTCCA GAGGTGCTAC TGGGAATGCC TTATGACCTT   1140

GCCATTGATA TGTGGTCCCT CGGGTGTATT TTGGTTGAAA TGCACACTGG AGAACCTCTG   1200

TTCAGTGGTG CCAATGAGGT AGATCAGATG AATAAAATAG TGGAAGTTCT GGGTATTCCA   1260

CCTGCTCATA TTCTTGACCA AGCACCAAAA GCAAGAAAGT TCTTTGAGAA GTTGCCAGAT   1320

GGCACTTGGA ACTTAAAGAA GACCAAAGAT GGAAAACGGG AGTACAAACC ACCAGGAACC   1380

CGTAAACTTC ATAACATTCT TGGAGTGGAA ACAGGAGGAC CTGGTGGGCG ACGTGCTGGG   1440

GAGTCAGGTC ATACGGTCGC TGACTACTTG AAGTTCAAAG ACCTCATTTT AAGGATGCTT   1500

GATTATGACC CCAAAACTCG AATTCAACCT TATTATGCTC TGCAGCACAG TTTCTTCAAG   1560

AAAACAGCTG ATGAAGGTAC AAATACAAGT AATAGTGTAT CTACAAGCCC CGCCATGGAG   1620

CAGTCTCAGT CTTCGGGCAC CACCTCCAGT ACATCGTCAA GCTCAGGTGG CTCATCGGGG   1680

ACAAGCAACA GTGGGAGAGC CCGGTCGGAT CCGACGCACC AGCATCGGCA CAGTGGTGGG   1740

CACTTCACAG CTGCCGTGCA GGCCATGGAC TGCGAGACAC ACAGTCCCCA GGTGCGTCAG   1800
```

-continued

```
CAATTTCCTG CTCCTCTTGG TTGGTCAGGC ACTGAAGCTC CTACACAGGT CACTGTTGAA       1860

ACTCATCCTG TTCAAGAAAC AACCTTTCAT GTAGCCCCTC AACAGAATGC ATTGCATCAT       1920

CACCATGGTA ACAGTTCCCA TCACCATCAC CACCACCACC ACCATCACCA CCACCATGGA       1980

CAACAAGCCT TGGGTAACCG GACCAGGCCA AGGGTCTACA ATTCTCCAAC GAATAGCTCC       2040

TCTACCCAAG ATTCTATGGA GGTTGGCCAC AGTCACCACT CCATGACATC CCTGTCTTCC       2100

TCAACGACTT CTTCCTCGAC ATCTTCCTCC TCTACTGGTA ACCAAGGCAA TCAGGCCTAC       2160

CAGAATCGCC CAGTGGCTGC TAATACCTTG GACTTTGGAC AGAATGGAGC TATGGACGTT       2220

AATTTGACCG TCTACTCCAA TCCCCGCCAA GAGACTGGCA TAGCTGGACA TCCAACATAC       2280

CAATTTTCTG CTAATACAGG TCCTGCACAT TACATGACTG AAGGACATCT GACAATGAGG       2340

CAAGGGGCTG ATAGAGAAGA GTCCCCCATG ACAGGAGTTT GTGTGCAACA GAGTCCTGTA       2400

GCTAGCTCGT GACTACATTG AAACTTGAGT TTGTTTCTTG TGTGTTTTTA TAGAAGTGGT       2460

GTTTTTTTTC CAAAAACAAA GTGCAAAGCT GCTTGAATCA GGAGGAGATT AACACACTGA       2520

ACCGCTACAA GAGGGCAAAG CTGATTTTTT TTTTAACTTG AAAAGATTGC AAAGGGACAT       2580

TGAAGTGTTT AAAAGAGCCA TGTCCAAACC CATCTTCATG GATAGCTCAG AGGTATCCTC       2640

TTTTTGCTCC CCCATTTTAA CTTGCCACAT CCCAGTCACA GTGGGGTTTT TTTGTCTTTC       2700

TATTCAGCAA AAGTTAATAT TCAGATGTTG GTCTTGGTCA TTTGCCAACT AATTTTAAAG       2760

TAAAAGGCAC TGCACATAAT TTGCATAAAG GGCCCCATGA GGGTGTTTTT TTTTTTTCTT       2820

TTTGTCCCCC CCATCCCCCT TTTTTTTTGT TTTGTTCTGT TTTGTTTTGG GTGGGAGGGT       2880

GGGAAATTTG GGTTTTTAAG TCCTCTAAAC ACACTTGGGC ACGGAAATGC AGTACTGTAA       2940

GGAANANGGA CCTCCAGCTT CCACAAACAC CATCTTCAGC TGTATGAAAG GGACGGTTGT       3000

GGTGAAGTTT GTCAGGCACA GTAAGCATGC TGAGTGGCGG GGATCAGAAC TCTCCTATCT       3060

GAACCTACTG AGGANCAAAG CAGCAATTAC ATGGATCCTG TGGCCNCCCC GTTGCAAAGC       3120

CCAGGAANAN AAGATGNACN TGACTGGTCT CCTAACCAAG TGCNCTGAAA ACCATCAACG       3180

GTCCGTCCTT GGCANTCCTG GGGAGTCTAA TTTGTGNC                              3218
```

(2) INFORMATION FOR SEQ ID NO:2:

(i) SEQUENCE CHARACTERISTICS:
        (A) LENGTH: 763 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:2:

```
Met His Thr Gly Gly Glu Thr Ser Ala Cys Lys Pro Ser Ser Val Arg
1               5                   10                  15

Leu Ala Pro Ser Phe Ser Phe His Ala Ala Gly Leu Gln Met Ala Gly
                20                  25                  30

Gln Met Pro His Ser His Gln Tyr Ser Asp Arg Gln Pro Asn Ile
            35                  40                  45

Ser Asp Gln Gln Val Ser Ala Leu Ser Tyr Ser Asp Gln Ile Gln Gln
        50                  55                  60

Pro Leu Thr Asn Gln Val Met Pro Asp Ile Val Met Leu Gln Arg Arg
65                  70                  75                  80

Met Pro Gln Thr Phe Arg Asp Pro Ala Thr Ala Pro Leu Arg Lys Leu
                85                  90                  95
```

-continued

```
Ser Val Asp Leu Ile Lys Thr Tyr Lys His Ile Asn Glu Val Tyr Tyr
            100                 105                 110

Ala Lys Lys Lys Arg Arg His Gln Gln Gly Gln Gly Asp Asp Ser Ser
        115                 120                 125

His Lys Lys Glu Arg Lys Val Tyr Asn Asp Gly Tyr Asp Asp Asp Asn
        130                 135                 140

Tyr Asp Tyr Ile Val Lys Asn Gly Glu Lys Trp Met Asp Arg Tyr Glu
145                 150                 155                 160

Ile Asp Ser Leu Ile Gly Lys Gly Ser Phe Gly Gln Val Val Lys Ala
                165                 170                 175

Tyr Asp Arg Val Glu Gln Glu Trp Val Ala Ile Lys Ile Ile Lys Asn
            180                 185                 190

Lys Lys Ala Phe Leu Asn Gln Ala Gln Ile Glu Val Arg Leu Leu Glu
        195                 200                 205

Leu Met Asn Lys His Asp Thr Glu Met Lys Tyr Tyr Ile Val His Leu
210                 215                 220

Lys Arg His Phe Met Phe Arg Asn His Leu Cys Leu Val Phe Glu Met
225                 230                 235                 240

Leu Ser Tyr Asn Leu Tyr Asp Leu Leu Arg Asn Thr Asn Phe Arg Gly
                245                 250                 255

Val Ser Leu Asn Leu Thr Arg Lys Phe Ala Gln Gln Met Cys Thr Ala
            260                 265                 270

Leu Leu Phe Leu Ala Thr Pro Glu Leu Ser Ile Ile His Cys Asp Leu
        275                 280                 285

Lys Pro Glu Asn Ile Leu Leu Cys Asn Pro Lys Arg Ser Ala Ile Lys
290                 295                 300

Ile Val Asp Phe Gly Ser Ser Cys Gln Leu Gly Gln Arg Ile Tyr Gln
305                 310                 315                 320

Tyr Ile Gln Ser Arg Phe Tyr Arg Ser Pro Glu Val Leu Leu Gly Met
                325                 330                 335

Pro Tyr Asp Leu Ala Ile Asp Met Trp Ser Leu Gly Cys Ile Leu Val
            340                 345                 350

Glu Met His Thr Gly Glu Pro Leu Phe Ser Gly Ala Asn Glu Val Asp
        355                 360                 365

Gln Met Asn Lys Ile Val Glu Val Leu Gly Ile Pro Pro Ala His Ile
370                 375                 380

Leu Asp Gln Ala Pro Lys Ala Arg Lys Phe Phe Glu Lys Leu Pro Asp
385                 390                 395                 400

Gly Thr Trp Asn Leu Lys Lys Thr Lys Asp Gly Lys Arg Glu Tyr Lys
                405                 410                 415

Pro Pro Gly Thr Arg Lys Leu His Asn Ile Leu Gly Val Glu Thr Gly
            420                 425                 430

Gly Pro Gly Gly Arg Arg Ala Gly Glu Ser Gly His Thr Val Ala Asp
        435                 440                 445

Tyr Leu Lys Phe Lys Asp Leu Ile Leu Arg Met Leu Asp Tyr Asp Pro
450                 455                 460

Lys Thr Arg Ile Gln Pro Tyr Tyr Ala Leu Gln His Ser Phe Phe Lys
465                 470                 475                 480

Lys Thr Ala Asp Glu Gly Thr Asn Thr Ser Asn Ser Val Ser Thr Ser
                485                 490                 495

Pro Ala Met Glu Gln Ser Gln Ser Ser Gly Thr Thr Ser Ser Thr Ser
            500                 505                 510
```

-continued

```
Ser Ser Ser Gly Gly Ser Ser Gly Thr Ser Asn Ser Gly Arg Ala Arg
            515                 520                 525

Ser Asp Pro Thr His Gln His Arg His Ser Gly Gly His Phe Thr Ala
    530             535                 540

Ala Val Gln Ala Met Asp Cys Glu Thr His Ser Pro Gln Val Arg Gln
545             550                 555                     560

Gln Phe Pro Ala Pro Leu Gly Trp Ser Gly Thr Glu Ala Pro Thr Gln
            565                 570                 575

Val Thr Val Glu Thr His Pro Val Gln Glu Thr Thr Phe His Val Ala
            580                 585                 590

Pro Gln Gln Asn Ala Leu His His His Gly Asn Ser Ser His His
            595             600             605

His His His His His His His His His Gly Gln Gln Ala Leu
    610                 615             620

Gly Asn Arg Thr Arg Pro Arg Val Tyr Asn Ser Pro Thr Asn Ser Ser
625             630                 635                     640

Ser Thr Gln Asp Ser Met Glu Val Gly His Ser His His Ser Met Thr
            645                 650             655

Ser Leu Ser Ser Ser Thr Thr Ser Ser Ser Thr Ser Ser Ser Ser Thr
            660             665             670

Gly Asn Gln Gly Asn Gln Ala Tyr Gln Asn Arg Pro Val Ala Ala Asn
            675             680             685

Thr Leu Asp Phe Gly Gln Asn Gly Ala Met Asp Val Asn Leu Thr Val
    690             695                 700

Tyr Ser Asn Pro Arg Gln Glu Thr Gly Ile Ala Gly His Pro Thr Tyr
705             710                 715                     720

Gln Phe Ser Ala Asn Thr Gly Pro Ala His Tyr Met Thr Glu Gly His
            725             730                 735

Leu Thr Met Arg Gln Gly Ala Asp Arg Glu Glu Ser Pro Met Thr Gly
            740             745             750

Val Cys Val Gln Gln Ser Pro Val Ala Ser Ser
        755             760
```

TRAF2-ASSOCIATED PROTEIN KINASE AND ASSAYS

This is a continuing application of U.S. Ser. No. 09/252,571, filed on Feb. 18, 1999, now U.S. Pat. No. 5,981,250 which is a divisional application of U.S. Ser. No. 08/677,862, filed Jul. 10, 1996, now U.S. Pat. No. 5,874,230, which are incorporated herein by reference.

FIELD OF THE INVENTION

The field of this invention is a class of human proteins involved in gene transcription.

BACKGROUND

Nuclear factor κB (NF-κB) is a homo- or heterodimer of members of the Rel family of transcriptional activators that is involved in the inducible expression of a wide variety of important cellular genes including numerous cytokines, cytokine receptors, major histocompatibility antigens, serum amyloid A protein, etc. as well as many viral genes including genes of HIV, SV40, cytomegalovirus, etc. Several tumor necrosis factor receptor-associated factor (TRAF) proteins have been identified and shown to be involved in the signaling of various cellular responses including cytotoxicity, anti-viral activity, immuno-regulatory activities and the transcriptional regulation of a number of genes.

Accordingly, the ability to exogenously modulate the activity of NF-κB and/or TRAF proteins would yield therapeutic application for numerous clinical indications. In addition, components of such pathways would provide valuable target reagents for automated, cost-effective, high throughput drug screening assays and hence would have immediate application in domestic and international pharmaceutical and biotechnology drug development programs. The present invention provides novel TRAF-2 associated kinase proteins which regulate TRAF-2 function, their use, e.g. in drug screens, and nucleic acids encoding the same.

RELEVANT LITERATURE

Kentrup et al. (1996) J. Biol. Chem 271, 3488–3495, report the existence of Dyrk, a rat protein kinase with sequence similarity with the human kinase disclosed herein.

SUMMARY OF THE INVENTION

The invention provides methods and compositions relating to a novel human TRAF2-associated protein kinase and gene. The subject kinase proteins comprise a functional domain of SEQ ID NO:2 distinguishable (e.g. in terms of sequence or function, such a binding specificity) from rodent homologs of the kinase. For example, SEQ ID NO:2, residues 1–158, 159–479 and 480–763 provide human-specific C, kinase and N domains, respectively. The invention also provides isolated hybridization probes and primers capable of specifically hybridizing with or amplifying the disclosed human kinase protein gene (SEQ ID NO:1), nucleic acids encoding the subject proteins, methods of making the subject proteins and nucleic acids, and methods of using the subject compositions in diagnosis (e.g. genetic hybridization screens for gene mutations), and in the biopharmaceutical industry (e.g. reagents for screening chemical libraries for lead compounds for a pharmacological agent useful in the diagnosis or treatment of disease associated with immune regulation).

DETAILED DESCRIPTION OF THE INVENTION

Figure 1:
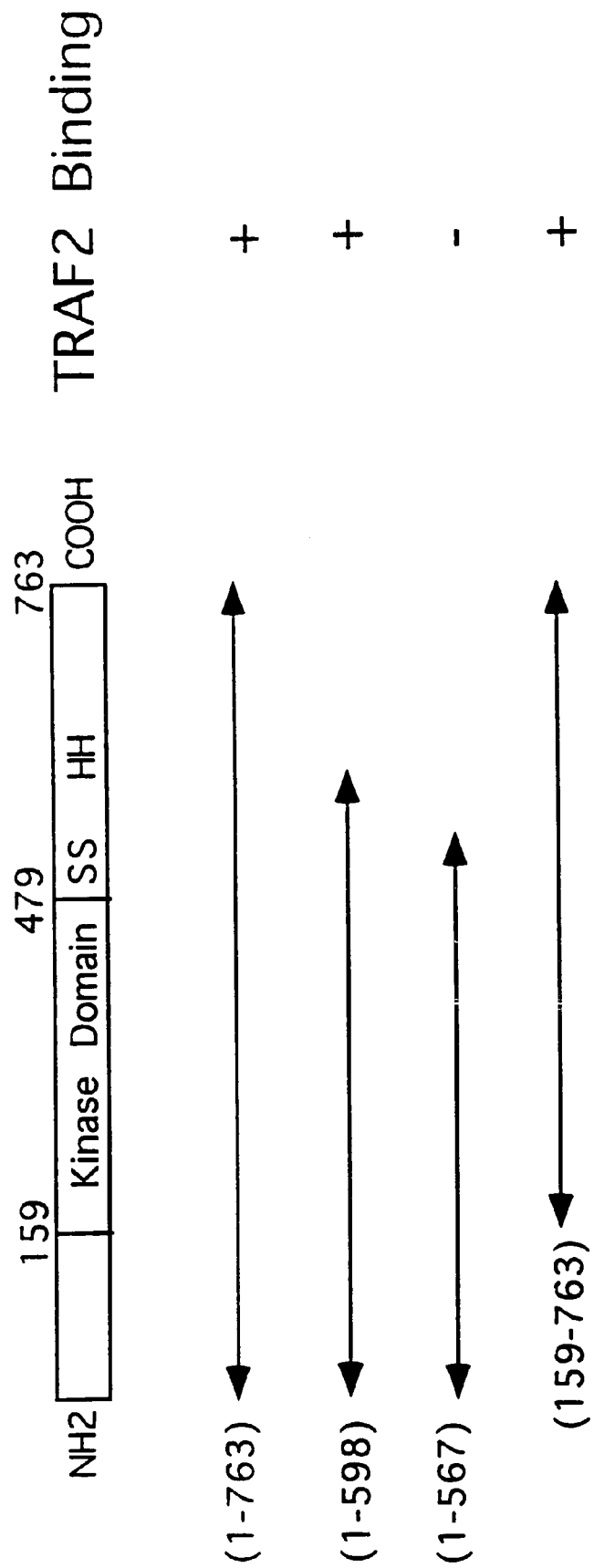
FIG. 1. Deletion mutant analysis of kinase proteins for TRAF2 binding.

The nucleotide sequence of a natural cDNA encoding a novel human TRAF2-associated protein kinase is shown as SEQ ID NO:1 and the full conceptual translate shown as SEQ ID NO:2. The kinase proteins of the invention include incomplete translates of SEQ ID NO:1 and deletion mutants of SEQ ID NO: 2, which translates and deletions mutants have amino acid sequence and binding specificity or function different from rodent homologs of the protein. For example, the domain bound by residues 159 (Tyr) through 479 (Phe) of SEQ ID NO:2 defines an active kinase domain which may be used, independently or joined to other domains, in the subject methods; see FIG. 1. Also, an internal domain within residues 159–598 of SEQ ID NO:2 includes a TRAF-2 binding domain. This domain finds use in methods involving kinase-TRAF-2 complexes and may be used independently as a regulator of TRAF-2 activity, as a reagent in kinase complex formation assays, etc.

The binding or function specificity of the subject proteins necessarily distinguishes, qualitatively and/or quantitatively, rodent homologs (e.g. the rat Dyrk gene product). This specificity is especially important for screens for lead pharmaceuticals (below). Binding or function specificity may be determined by convenient in vitro, cell-based, or in vivo assays. Preferred proteins have kinase activity (e.g. autophosphorylate), specifically bind TRAF2 or modulate NF-κB activation. Such activity or function may be demonstrated in in vitro binding assays, in cell culture (e.g. cell transfections) or in animals (e.g. in vivo gene therapy, transgenics). Generally, binding specificity is shown by kinase activity, by binding equilibrium constants (usually at least about $10^7$ $M^{-1}$, preferably at least about $10^8$ $M^{-1}$, more preferably at least about $10^9$ $M^{-1}$) with natural binding targets such as hTRAF2 or nonnatural targets such as specific antibodies, by the ability of the subject protein to elicit a specific antibody in a rodent or rabbit (i.e. an antibody which distinguishes the subject proteins from rodent homologs), etc.

The claimed proteins are isolated or pure and are typically recombinantly produced. An "isolated" protein is unaccompanied by at least some of the material with which it is associated in its natural state, preferably constituting at least about 0.5%, and more preferably at least about 5% by weight of the total protein in a given sample and a pure protein constitutes at least about 90%, and preferably at least about 99% by weight of the total protein in a given sample. A wide variety of molecular and biochemical methods are available for generating, expressing and purifying the subject compositions, see e.g. Molecular Cloning, A Laboratory Manual (Sambrook, et al. Cold Spring Harbor Laboratory), Current Protocols in Molecular Biology (Eds. Ausubel, et al., Greene Publ. Assoc., Wiley-Interscience, NY) or that are otherwise known in the art.

The invention provide binding agents specific to the subject kinase proteins including substrates, agonists, antagonists, natural intracellular binding targets, etc., methods of identifying and making such agents, and their use in diagnosis, therapy and pharmaceutical development. For example, specific binding agents are useful in a variety of diagnostic and therapeutic applications, especially where disease or disease prognosis is associated with improper utilization of a pathway involving the subject proteins, e.g. NF-κB activation. Novel specific binding agents include specific antibodies and other natural intracellular binding agents identified with assays such as one-, two- and threehybrid screens, non-natural intracellular binding agents identified in screens of chemical libraries such as described below, etc.

The invention also provides nucleic acids encoding the subject proteins, which nucleic acids may be part of expression vectors and may be incorporated into recombinant cells for expression and screening, transgenic animals for functional studies (e.g. the efficacy of candidate drugs for disease associated with signal transduction mediated by the subject kinase proteins), etc., and nucleic acid hybridization probes and replication/amplification primers having a cDNA specific sequence contained in SEQ ID NO:1 and sufficient to effect specific hybridization thereto (i.e. specifically hybridize with SEQ ID NO:1 in the presence of natural cDNAs encoding rodent homologs, eg. rat Dyrk cDNA (Kentrup et al., 1996, supra).

The subject nucleic acids are isolated, i.e. unaccompanied by at least some of the material with which it is associated in its natural state, preferably constituting at least about 0.5%, preferably at least about 5% by weight of total nucleic acid present in a given fraction, and usually recombinant, meaning they comprise a sequence joined to a nucleotide other than that which it is joined to on a natural chromosome. Nucleic acids comprising the nucleotide sequence of SEQ ID NO: 1 or fragments thereof, contain such sequence or fragment at a terminus, immediately flanked by a sequence other than that which it is joined to on a natural chromosome, or flanked by a native flanking region fewer than 10 kb, preferably fewer than 2 kb, which is immediately flanked by a sequence other than that which it is joined to on a natural chromosome. The subject nucleic acids find a wide variety of applications including use as translatable transcripts, hybridization probes, PCR primers, diagnostic nucleic acids, etc.; use in detecting the presence of the subject genes and gene transcripts and in detecting or amplifying nucleic acids encoding additional homologs and structural analogs. In diagnosis, the hybridization probes and/or primers find use in identifying wild-type and mutant alleles in clinical and laboratory samples. Mutant alleles are used to generate reagents e.g. allele-specific oligonucleotides (ASO), for high-throughput clinical diagnoses.

The invention provides efficient methods of identifying agents, compounds or lead compounds for agents active at the level of cellular function modulated by the disclosed protein kinases. Generally, these screening methods involve assaying for compounds which modulate interaction with a natural binding target. A wide variety of assays for binding agents are provided including labeled in vitro kinase assays, protein-protein binding assays, immunoassays, cell based assays, etc. The methods are amenable to automated, cost-effective high throughput screening of chemical libraries for lead compounds. Identified reagents find use in the pharmaceutical industries for animal and human trials; for example, the reagents may be derivatized and rescreened in in vitro and in vivo assays to optimize activity and minimize toxicity for pharmaceutical development. Target indications may include infection, genetic disease, cell growth and regulatory disfunction, such as neoplasia, inflammation, hypersensitivity, etc.

In vitro binding assays employ a mixture of components including a subject protein kinase, which may be part of a fusion product with another peptide or polypeptide, e.g. a polypeptide that is capable of providing or enhancing protein-protein binding, stability under assay conditions, or a tag for detection or anchoring, etc. The assay mixtures comprise a natural intracellular specific-binding target, e.g. a substrate, such as TRAF2. A pseudosubstrate may be used or modified (e.g. A to S/T substitutions) to generate effective substrates for use in the subject kinase assays. While native binding targets may be used, it is frequently preferred to use portions (e.g. peptides, nucleic acid fragments) or analogs thereof so long as the portion or analog provides binding affinity and avidity to the subject protein kinase conveniently measurable in the assay. The assay mixture also comprises a candidate pharmacological agent. Candidate agents encompass numerous chemical classes, though typically they are organic compounds; preferably small organic compounds and are obtained from a wide variety of sources including libraries of synthetic or natural compounds. A variety of other reagents may also be included in the mixture. These include reagents like salts, buffers, neutral proteins, e.g. albumin, detergents, etc. which may be used to facilitate optimal binding and/or reduce non-specific or background interactions, etc. Also, reagents that otherwise improve the efficiency of the assay, such as protease inhibitors, nuclease inhibitors, antimicrobial agents, etc. may be used.

The resultant mixture is incubated under conditions whereby, but for the presence of the candidate pharmacological agent, the kinase protein specifically binds the binding target, with a reference binding affinity. The mixture components can be added in any order that provides for the requisite bindings and incubations may be performed at any temperature which facilitates optimal binding, typically between 4° and 40° C., more commonly between 15° and 40° C. Incubation periods are likewise selected for optimal binding but also minimized to facilitate rapid, high-throughput screening, and are typically between 0.1 and 10 hours, preferably less than 5 hours, more preferably less than 2 hours.

After incubation, the agent-biased binding between the kinase protein and one or more binding targets is detected by any convenient way. For cell-free binding type assays, a separation step is often used to separate bound from unbound components. Separation may be effected by precipitation (e.g. TCA precipitation, immunoprecipitation, etc.), immobilization (e.g on a solid substrate), etc., followed by washing by, for examples, membrane filtration (e.g. Whatman's P-81 ion exchange paper, Polyfiltronic's hydrophobic GFC membrane, etc.), gel chromatography (e.g. gel filtration, affinity, etc.). For kinase assays, binding is detected by a change in the kinase-induced phosphorylation of the substrate.

Detection may be effected in any convenient way. For cell-free binding assays, one of the components usually comprises or is coupled to a label. A wide variety of labels may be employed—essentially any label that provides for detection of bound protein. The label may provide for direct detection as radioactivity, luminescence, optical or electron density, etc. or indirect detection such as an epitope tag, an enzyme, etc. A variety of methods may be used to detect the label depending on the nature of the label and other assay components. For example, the label may be detected bound to the solid substrate or a portion of the bound complex containing the label may be separated from the solid substrate, and thereafter the label detected. Labels may be directly detected through optical or electron density, radiative emissions, nonradiative energy transfers, etc. or indirectly detected with antibody conjugates, etc. For example, in the case of radioactive labels, emissions may be detected directly, e.g. with particle counters or indirectly, e.g. with scintillation cocktails and counters.

A difference in the binding affinity of the kinase protein to the target in the absence of the agent as compared with the binding affinity in the presence of the agent indicates that the agent modulates the binding of the kinase protein to the binding target. Analogously, in the cell-based transcription assay also described below, a difference in the transcriptional induction in the presence and absence of an agent indicates the agent modulates transcription induced by the subject kinase protein. A difference, as used herein, is statistically significant and preferably represents at least a 50%, more preferably at least a 90% difference.

The following experiments and examples are offered by way of illustration and not by way of limitation.

EXPERIMENTAL

A human kinase protein was initially identified in immunoprecipitates of TRAF2. Coprecipitating proteins were purified and subject to peptide sequencing. The resultant sequence data were used to design oligonucleotide probe and primers to isolate human cDNA clones. Identification was confirmed by overexpressing a full-length myc-tagged kinase-encoding cDNA in human 293 cells cotransfected with FLAG-tagged TRAF2 and immunoprecipitating the lysates with anti-FLAG then western blot analysis with anti-myc. A yeast two-hybrid system was also used to confirm TRAF2 binding and for deletion mutagenesis analysis of kinase. These experiments revealed that residues 1–763, residues 1–598 and residues 159–763 are each sufficient to mediate TRAF2 binding, while residues 1–567 is not. Human kinase peptides derived from the 567–598 are able to inhibit kinase-TRAF2 binding. Sequence analysis further define a kinase domain of residues 159–479. Recombinant kinase was prepared by over-expressing GST fusion proteins in *E. coli* and baculavirus expression systems.

EXAMPLES

1. Protocol for Autophosphorylation Assay
   A. Reagents
   Neutralite Avidin: 20 µg/ml in PBS.
   kinase: $10^{-8}$–$10^{-5}$ M biotinylated kinase (SEQ ID NO:2) at 20 µg/ml in PBS.
   Blocking buffer: 5% BSA, 0.5% Tween 20 in PBS; 1 hour at room temperature.
   Assay Buffer: 100 mM KCl, 10 mM $MgCl_2$, 1 mM $MnCl_2$, 20 mM HEPES pH 7.4, 0.25 mM EDTA, 1% glycerol, 0.5% NP-40, 50 mM BME, 1 mg/ml BSA, cocktail of protease inhibitors.
   [$^{32}$P]γ-ATP 10×stock: $2\times10^{-5}$ M cold ATP with 100 µCi [$^{32}$P]γ-ATP. Place in the 4° C. microfridge during screening.
   Protease inhibitor cocktail (1000×): 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2 mM NaVo3 (Sigma #S-6508) in 10 ml of PBS.
   B. Preparation of Assay Plates
   Coat with 120 µl of stock N Avidin per well overnight at 4° C.
   Wash 2 times with 200 µl PBS.
   Block with 150 µl of blocking buffer.
   Wash 2 times with 200 µl PBS.
   C. Assay
   Add 40 µl assay buffer/well.
   Add 40 µl biotinylated kinase (0.1–10 pmoles/40 ul in assay buffer)
   Add 10 µl compound or extract.
   Add 10 µl [$^{32}$P]γ-ATP 10×stock.
   Shake at 25° C. for 15 minutes.
   Incubate additional 45 minutes at 25° C.
   Stop the reaction by washing 4 times with 200 µl PBS.
   Add 150 µl scintillation cocktail.
   Count in Topcount.
   D. Controls for All Assays (Located on Each Plate)
   a. Non-specific binding
   b. cold ATP at 80% inhibition.

2. Protocol for Kinase Protein—hTRAF2 Complex Formation Assay
   A. Reagents
   Neutralite Avidin: 20 µg/ml in PBS.
   Blocking buffer: 5% BSA, 0.5% Tween 20 in PBS; 1 hour at room temperature.
   Assay Buffer: 100 mM KCl, 10 mM $MgCl_2$, 1 mM $MnCl_2$, 20 mM HEPES pH 7.6, 0.25 mM EDTA, 1% glycerol, 0.5% NP-40, 50 mM β-mercaptoethanol, 1 mg/mil BSA, cocktail of protease inhibitors.
   $^{33}$P kinase protein 10×stock: $10^{-8}$–$10^{-6}$ M "cold" kinase protein (SEQ ID NO:2, residues 159–598) supplemented with 200,000–250,000 cpm of labeled kinase protein (Beckman counter). Place in the 4° C. microfridge during screening.
   Protease inhibitor cocktail (1000×): 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2 mM $NaVo_3$ (Sigma #S-6508) in 10 ml of PBS.
   hTRAF2: $10^{-8}$–$10^{-5}$ M biotinylated hTRAF2 in PBS.
   B. Preparation of Assay Plates
   Coat with 120 µl of stock N-Avidin per well overnight at 4° C.
   Wash 2 times with 200 µl PBS.
   Block with 150 µl of blocking buffer.
   Wash 2 times with 200 µl PBS.
   C. Assay
   Add 40 µl assay buffer/well.
   Add 10 µl compound or extract.
   Add 10 µl $^{33}$P-kinase protein (20,000–25,000 cpm/0.1–10 pmoles/well=$10^{-9}$–$10^{-7}$ M final concentration).
   Shake at 25° C. for 15 minutes.
   Incubate additional 45 minutes at 25° C.
   Add 40 µl biotinylated hTRAF2 (0.1–10 pmoles/40 ul in assay buffer)
   Incubate 1 hour at room temperature.
   Stop the reaction by washing 4 times with 200 µl PBS.
   Add 150 µl scintillation cocktail.
   Count in Topcount.
   D. Controls for All Assays (Located on Each Plate)
   a. Non-specific binding
   b. Soluble (non-biotinylated hTRAF2) at 80% inhibition.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated human tumor necrosis factor receptor associated factor number two associated kinase protein comprising a domain selected from the group consisting of residues 1–158, 159–479 and 480–763, as set forth in SEQ ID NO:2.

2. The protein of claim 1, comprising a domain consisting of residues 1–158, as set forth in SEQ ID NO:2.

3. The protein of claim 1, comprising a domain consisting of residues 159–479, as set forth in SEQ ID NO:2.

4. The protein of claim 1, comprising a domain consisting of residues 480–763, as set forth in SEQ ID NO:2.

5. The protein of claim 1, wherein said protein comprises SEQ ID NO:2.

* * * * *